(12) United States Patent
Sertel et al.

(10) Patent No.: US 10,473,587 B2
(45) Date of Patent: Nov. 12, 2019

(54) ON-CHIP, WIDEBAND, DIFFERENTIALLY FED ANTENNAS WITH INTEGRATED BIAS STRUCTURES

(71) Applicant: OHIO STATE INNOVATION FOUNDATION, Columbus, OH (US)

(72) Inventors: Kubilay Sertel, Hilliard, OH (US); Georgios C. Trichopoulos, Tempe, AZ (US); Cosan Caglayan, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 209 days.

(21) Appl. No.: 15/598,844

(22) Filed: May 18, 2017

(65) Prior Publication Data

US 2019/0017931 A1    Jan. 17, 2019

Related U.S. Application Data

(60) Provisional application No. 62/338,570, filed on May 19, 2016.

(51) Int. Cl.
*G01R 31/302* (2006.01)
*G01N 21/3581* (2014.01)
(Continued)

(52) U.S. Cl.
CPC ..... *G01N 21/3581* (2013.01); *G01R 1/06772* (2013.01); *G01R 31/2822* (2013.01);
(Continued)

(58) Field of Classification Search
CPC ........... G01N 21/3581; G01N 21/3563; G01R 31/2822; G01R 31/3025; G01R 31/311;
(Continued)

(56) References Cited

U.S. PATENT DOCUMENTS 9,488,572 B2    11/2016  Sertel et al.
2014/0347073 A1*  11/2014  Brown ............... G01N 21/3581
                                                                 324/637
2015/0102225 A1*  4/2015  Sertel ................. G01R 31/2822
                                                                 250/341.5

OTHER PUBLICATIONS

Bockelman, et al., Pure-mode network analyzer for on-wafer measurements of mixed-mode S-parameters of differential circuits. *IEEE Transactions on Microwave Theory and Techniques*, vol. 45(7), pp. 1071-1077 (1997).

(Continued)

*Primary Examiner* — Minh N Tang
(74) *Attorney, Agent, or Firm* — Fay Sharpe LLP

(57) ABSTRACT

Terahertz (THz) or millimeter wave (mmW) band characterization of a differential-mode device under test (DUT) is performed using a non-contact probing setup based on an integrated circuit that includes the on-chip DUT and an on-chip test fixture as follows. A differential transmission line pair is operatively coupled with the DUT. A first differential antenna pair at a first end of the transmission line pair has a first antenna connected only with the first transmission line and a second antenna connected only with the second transmission line. A second differential antenna pair is likewise connected with a second end of the differential transmission line pair. A THz or mmW transmitter radiates a probe THz or mmW beam to the first differential antenna pair, and an electronic analyzer receives a THz or mmW signal radiated by the second differential antenna pair responsive to the radiation of the probe THz or mmW beam to the first differential antenna pair, thus enabling no-contact S-parameter measurements for characterizing differential-mode, on-wafer, active or passive devices and integrated circuits.

17 Claims, 14 Drawing Sheets

(51) Int. Cl.
G01R 31/28 (2006.01)
H04L 25/02 (2006.01)
G01R 1/067 (2006.01)
H01P 5/10 (2006.01)
H01Q 25/02 (2006.01)
H01Q 1/36 (2006.01)
H01Q 15/23 (2006.01)
H01Q 19/06 (2006.01)
H01Q 19/13 (2006.01)
G01R 31/303 (2006.01)
G01R 31/311 (2006.01)
H04L 25/08 (2006.01)
H01P 3/00 (2006.01)

(52) U.S. Cl.
CPC ....... G01R 31/303 (2013.01); G01R 31/3025 (2013.01); G01R 31/311 (2013.01); H01P 5/10 (2013.01); H01Q 1/36 (2013.01); H01Q 15/23 (2013.01); H01Q 19/062 (2013.01); H01Q 19/132 (2013.01); H01Q 25/02 (2013.01); H04L 25/0276 (2013.01); H01P 3/003 (2013.01); H04L 25/085 (2013.01)

(58) Field of Classification Search
CPC .... H04L 25/0276; H04L 25/085; H01P 3/003; H01P 5/02; H01P 5/10
See application file for complete search history.

(56) References Cited

OTHER PUBLICATIONS

Caglayan, et al., "Non-Contact Differential-Mode On-Wafer Device Characterization in the mmW and THz Bands," *2016 IEEE MTT-S International Microwave Symposium (IMS)*, pp. 1-3 (2016).

Caglayan, et al., "Repeatability performance of non-contact probes in the 500-750GHz band," *2015 85th Microwave Measurement Conference (ARFTG)*, pp. 1-3 (2015).

Chen, et al., "Terahertz Micromachined On-Wafer Probes: Repeatability and Reliability," *IEEE Transactions on Microwave Theory and Techniques*, vol. 60(9), pp. 2894-2902 (2012).

Dambrine, et al., "A new method for determining the FET small-signal equivalent circuit," *IEEE Transactions on Microwave Theory and Techniques*, vol. 36(7), pp. 1151-1159 (1988).

Filipovic, et al., "Double-slot antennas on extended hemispherical and elliptical silicon dielectric lenses," *IEEE Transactions on Microwave Theory and Techniques*, vol. 41(10), pp. 1738-1749 (1993).

Jung, et al., "A New Characterization and Calibration Method for 3-dB-Coupled On-Wafer Measurements," *IEEE Transactions on Microwave Theory and Techniques*, vol. 56(5), pp. 1193-1200 (2008).

Jung, et al., "Marchand Balun Embedded Probe," *IEEE Transactions on Microwave Theory and Techniques*, vol. 56(5), pp. 1207-1214 (2008).

Karisan, et al., "Lumped-Element Equivalent Circuit Modeling of Millimeter-Wave HEMT Parasitics Through Full-Wave Electromagnetic Analysis," *IEEE Transactions on Microwave Theory and Techniques*, vol. 64(5), pp. 1419-1430 (2016).

Kim, et al., "Analysis and design of impedance transformed balun integrated microwave probe for differential circuit measurement," *2008 IEEE MTT-S International Microwave Symposium Digest*, pp. 56-61 (2008).

Li, et al., "A SiGe Envelope-Tracking Power Amplifier With an Integrated CMOS Envelope Modulator for Mobile WiMAX/3GPP LTE Transmitters," *IEEE Transactions on Microwave Theory and Techniques*, vol. 59(10), pp. 2525-2536 (2011).

Liu, et al., "Millimeter-Wave Self-Healing Power Amplifier With Adaptive Amplitude and Phase Linearization in 65-nm CMOS," *IEEE Transactions on Microwave Theory and Techniques*, vol. 60(5), pp. 1342-1352 (2012).

Ojefors, et al., "Subharmonic 220- and 320-GHz SiGe HBT Receiver Front-Ends," *IEEE Transactions on Microwave Theory and Techniques*, vol. 60(5), pp. 1397-1404 (2012).

Zhang, et al., "A W-band balun integrated probe with common mode matching network," *2014 IEEE MTT-S International Microwave Symposium (IMS)*, pp. 1-4 (2014).

Zwick, T. and Pfeiffer, U.R. Pure-mode network analyzer concept for on-wafer measurements of differential circuits at millimeter-wave frequencies. *IEEE Transactions on Microwave Theory and Techniques*, vol. 53(3), pp. 934-937 (2005).

Caglayan, Cosan, "Non-Contact Probes for On-Wafer Characterization of Sub- Millimeter-Wave Devices and Integrated Circuits," published in IEEE Transactions on Microwave Theory and Techniques, vol. 62(11), pp. 2791-2801 (2014).

* cited by examiner

Differential-Mode Currents

ON-CHIP, WIDEBAND, DIFFERENTIALLY FED ANTENNAS WITH INTEGRATED BIAS STRUCTURES

This application claims the benefit of U.S. Provisional Application No. 62/338,570 filed May 19, 2016. U.S. Provisional Application No. 62/338,570 filed May 19, 2016 is incorporated by reference herein in its entirety.

This invention was made with Government support under Office of Naval Research Multidisciplinary University Research Initiative (ONR MURI) grant/contract no. N00014-11-1-0077, awarded by the Office of Naval Research (ONR). The government has certain rights in the invention.

BACKGROUND

Differential topologies offer key advantages for integrated devices such as mixers, voltage-controlled oscillators and amplifiers, providing better speed, frequency response and noise performance. Moreover, "balanced" antenna topologies are useful for wideband, efficient, and well-isolated transceiver front- and back-ends. As such, differential-mode circuit topologies are widely utilized for the design of high performance microwave monolithically integrated circuits (MMICs) spanning RF to lower-mmW bands. Nevertheless, for higher-mmW and sub-mmW bands (>100 GHz), design and characterization of differential-mode on-chip devices and circuits have long been a technical challenge. Therefore, despite their advantages, research and development of differential terahertz monolithically integrated circuits (TMICs) are impeded by the lack of measurement and characterization tools.

For differential-mode on-wafer device characterization, dual-tip coplanar, coaxial probes are interfaced with either four-port, dual-source VNAs (vector network analyzer) or two-port VNAs are used in conjunction with hybrids/couplers for a pure-mode VNA (PMVNA). While dual-source, four-port VNAs are limited by the deteriorating phase noise at higher frequencies, pure-mode VNA concepts are limited by the availability of components and interconnect elements beyond 110 GHz.

As an alternative, balun-integrated probes were introduced for pure differential-mode measurements. In such micro-machined probe architectures, a Marchand-type balun is fabricated onto the dual, coplanar contact probe tip membrane. The balun converts the conventional test signal injected by the VNA into an on-wafer, pure differential-mode excitation, while suppressing any common mode signals emerging from the discontinuities in the fixture or the on-chip device under test. Evidently, this approach involves multilayered lithography to fabricate the balun on the probe membrane, leading to increased manufacturing and maintenance costs. Furthermore, most recent prototypes reported in the literature cover only up to 110 GHz, leaving much of the sub-mmW spectrum out of reach.

Alternatively, a balun can be fabricated on the same wafer as the device under test (DUT) and conventional, single-tip probes can be used to characterize the response. Nevertheless, fabrication of such on-wafer baluns also require a fairly complex process, adding to the overall cost and introducing fabrication uncertainties such as yield. Moreover, such on-wafer baluns are needed for each and every device under test, leading to prohibitive costs.

BRIEF DESCRIPTION

In some illustrative embodiments disclosed as illustrative examples herein, an apparatus is disclosed for performing terahertz (THz) or millimeter wave (mmW) characterization. An integrated circuit includes an on-chip device under test (DUT) and an on chip test fixture. The fixture includes a differential transmission line pair comprising parallel first and second transmission lines operatively coupled with the DUT, a first differential antenna pair connected with a first end of the differential transmission line pair and including a first antenna connected only with the first transmission line and a second antenna connected only with the second transmission line, and a second differential antenna pair connected with a second end of the differential transmission line pair and including a third antenna connected only with the first transmission line and a fourth antenna connected only with the second transmission line. A THz or mmW transmitter is arranged to radiate a probe THz or mmW beam to the first differential antenna pair of the test fixture. An electronic analyzer is configured to receive a THz or mmW signal radiated by the second differential antenna pair of the test fixture responsive to the radiation of the probe THz or mmW beam to the first differential antenna pair of the test fixture.

In some illustrative embodiments disclosed as illustrative examples herein, a method is disclosed for performing THz or mmW characterization of a device under test (DUT) comprising a component of an integrated circuit. The method comprises: exciting the DUT in differential mode by radiating a probe THz or mmW beam to a first on-chip differential antenna pair of the integrated circuit wherein the first on-chip differential antenna pair comprises a common mode-suppressing balun; and receiving a THz or mmW differential signal generated by the DUT in response to the exciting wherein the THz or mmW signal is received via radiation by a second on-chip differential antenna pair of the integrated circuit wherein the second on-chip differential antenna pair comprises a common mode-suppressing balun.

In some illustrative embodiments disclosed as illustrative examples herein, an integrated circuit comprises an on-chip device under test (DUT) and on-chip differential-mode non-contact probes. The probes include a differential transmission line pair comprising parallel first and second transmission lines operatively coupled with the DUT, a first differential antenna pair connected with a first end of the differential transmission line pair and including a first antenna connected only with the first transmission line and a second antenna connected only with the second transmission line, and a second differential antenna pair connected with a second end of the differential transmission line pair and including a third antenna connected only with the first transmission line and a fourth antenna connected only with the second transmission line.

BRIEF DESCRIPTION OF THE DRAWINGS

Unless otherwise noted, the drawings are not to scale or proportion. The drawings are provided only for purposes of illustrating preferred embodiments and are not to be construed as limiting.

FIG. 3 illustrates a differential mode three-dimensional (3D) polar plot of the radiation and/or reception pattern operating in differential mode. FIG. 4 shows the corresponding common-mode 3D radiation pattern operating in common-mode. FIG. 5 plots the E-plane patterns of common- and differential-mode excitation, and FIG. 6 plots the corresponding H-plane patterns, illustrating the difference in directivity levels.

DETAILED DESCRIPTION OF PREFERRED EMBODIMENTS

In some illustrative embodiments disclosed herein, test fixtures are provided which include an on-chip antenna design that concurrently functions as a 180° hybrid balun, extending the non-contact probing technique presented in, e.g. Sertel et al., U.S. Pat. No. 9,488,572 to differential-mode characterization of on-wafer devices and integrated circuits. The illustrative antenna design is based on a "balanced" dual-slot butterfly topology integrated onto the focal plane of an extended hemispherical lens. Two such antennas are fabricated at the input and output ports of the on-chip device under test and are used to inject and receive the test signals from VNA ports quasi-optically.

Figure 1:
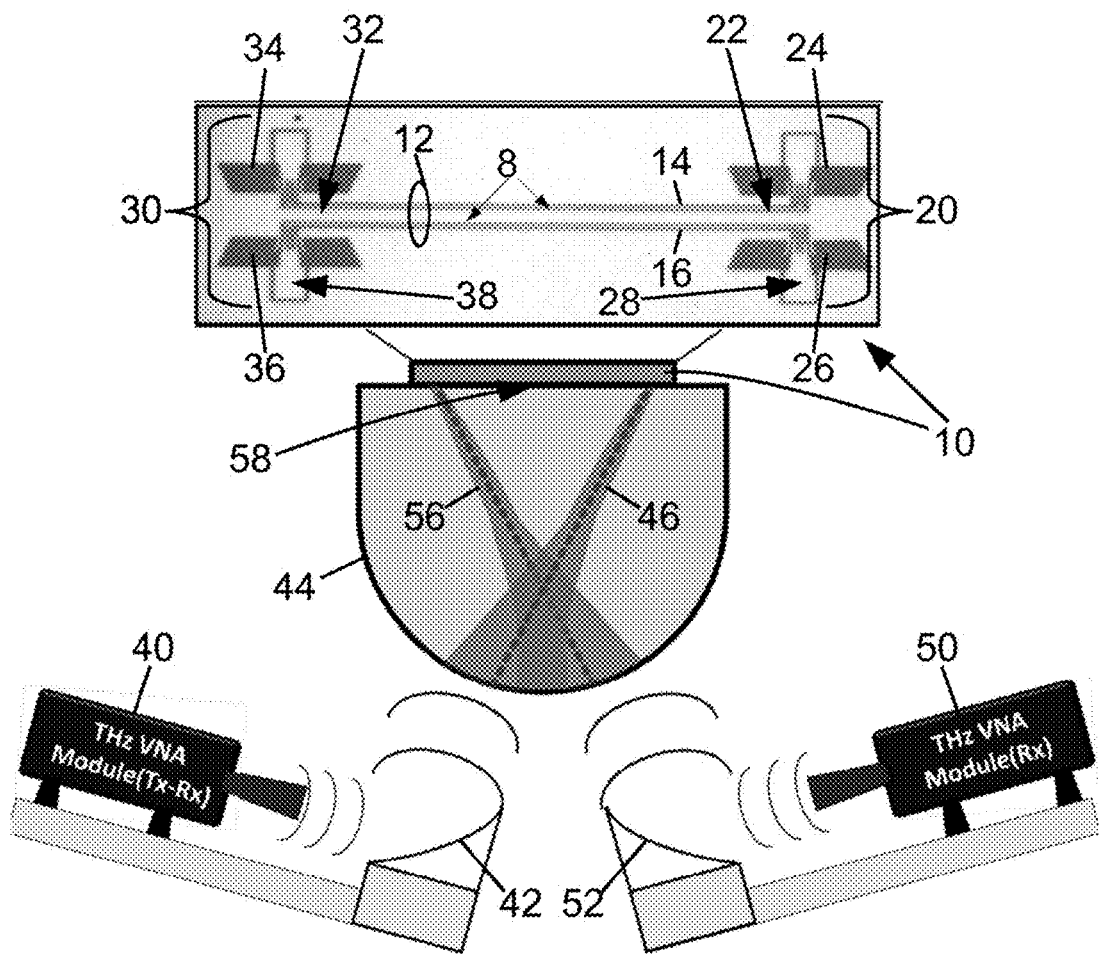
FIG. 1 diagrammatically shows an illustrative test setup including an integrated circuit comprising an on-chip device under test (DUT) and on-chip differential-mode non-contact probes. The probes include a differential transmission line pair operatively coupled with the DUT, and first and second differential antenna pairs connected with respective first and second ends of the differential transmission line pair.

With reference to FIG. 1, an illustrative test setup is shown. A test wafer 10 has an integrated circuit including an on-chip device under test (DUT, not shown in FIG. 1 but suitably connecting at indicated uncoupled coplanar waveguide ports 8) and an on-chip test fixture including: (1) a differential transmission line pair 12 comprising a first transmission line 14 and a second transmission line 16 arranged in parallel and operatively coupled with the DUT; (2) a first differential antenna pair 20 is connected with a first end 22 of the differential transmission line pair 12 and includes a first antenna 24 connected only with the first transmission line 14 and a second antenna 26 connected only with the second transmission line 16; and (3) a second differential antenna pair 30 connected with a second end 32 of the differential transmission line pair 12 and including a third antenna 34 connected only with the first transmission line 14 and a fourth antenna 36 connected only with the second transmission line 16. The first differential antenna pair 20 may also optionally include DC bias pads 28, and similarly the second differential antenna pair 30 may also optionally include DC bias pads 38. A THz or mmW transmitter 40 (illustrative THz VNA module operating as a transceiver) is arranged (by way of a parabolic mirror 42 and an extended hemispherical lens 44) to radiate a probe THz or mmW beam 46 to the first differential antenna pair 20 of the test fixture. An electronic analyzer 50 (illustrative THz VNA module operating as a receiver) is configured (by way of the extended hemispherical lens 44 and a parabolic mirror 52) to receive a THz or mmW signal 56 radiated by the second differential antenna pair 30 of the test fixture responsive to the radiation of the probe THz or mmW beam 46 to the first differential antenna pair 20 of the test fixture.

As noted above, the non-contact probe scheme used here was previously demonstrated for on-chip characterization of single-ended devices and circuits. E.g. Sertel et al., U.S. Pat. No. 9,488,572. With the antenna structure disclosed herein that effectively performs as a 180° hybrid balun, the same setup can be used to convert the VNA signal into a pure-differential mode excitation on the wafer 10. As such, the need for an on-chip or probe-integrated balun is eliminated. The approach disclosed herein enables non-contact probing of differential devices and ICs (referred to herein as the device under test, or "DUT") with ease in the high mmW and THz bands.

The non-contact probes disclosed herein employ quasi-optical coupling of VNA signals 46, 56 onto the coplanar waveguide (CPW) environment of the device under test, via the planar on-chip antennas 24, 26, 34, 36 situated on the test wafer 10 which is placed over the hyperhemispherical (or the extended hemispherical) lens 44. The extended hemispherical lens 44 used in the illustrative non-contact probes is made of high-resistivity Silicon and allows for efficient coupling of VNA signals into the on-wafer CPW environment of the device under test. For best coupling efficiency, the refractive index of the wafer 10 should be similar to that of high-resistivity Silicon lens. This is indeed the case for common wafer materials, such as Si ($\varepsilon_r$=11.7), GaAs ($\varepsilon_r$=10.9), GaN ($\varepsilon_r$=8.9), etc. In order to provide differential-mode device characterization, the on-chip antennas 24, 26, 34, 36 interface with the on-chip differential co-planar waveguide pair 12.

Figure 2:
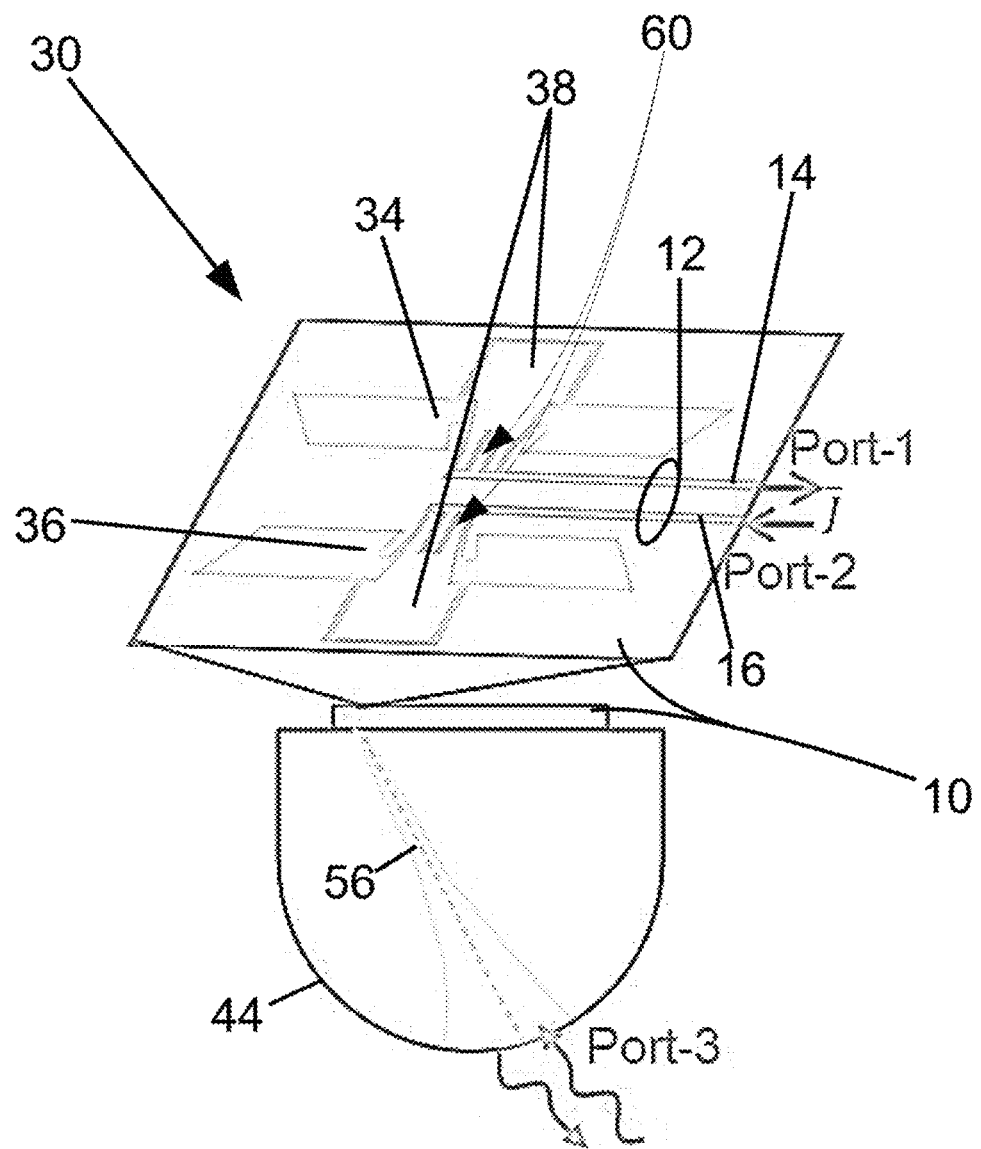
FIG. 2 diagrammatically shows an enlarged perspective view of the second differential antenna pair of the test setup of FIG. 1.

With reference to FIG. 2, an enlarged perspective view of the second differential antenna pair 30 is shown. (The first differential antenna pair 20 is analogous). The two slots (i.e. antenna 34, 36) of the antenna pair 30 can be fed individually via the symmetric pair 12 of dual-feed co-planar waveguide (CPW) lines 14, 16. This "baluntenna" topology is shown in FIG. 1 where the two CPW lines 14, 16 are parallel to the antenna slots and both lines are impedance matched to the radiating slots. This is merely one illustrative baluntenna configuration among other alternatives; this particular topology was chosen to maximize isolation between the individual on-wafer ports. In some actually constructed examples, the overall width of the 50Ω coplanar line was kept as small as possible and the CPW pair 14, 16 was kept far apart, without intruding the antenna slots. The lengths and distance between the slots were carefully designed to achieve a highly-directive radiation pattern over the entire operation bandwidth, covering the H-band (220-325 GHz).

Figure 3:
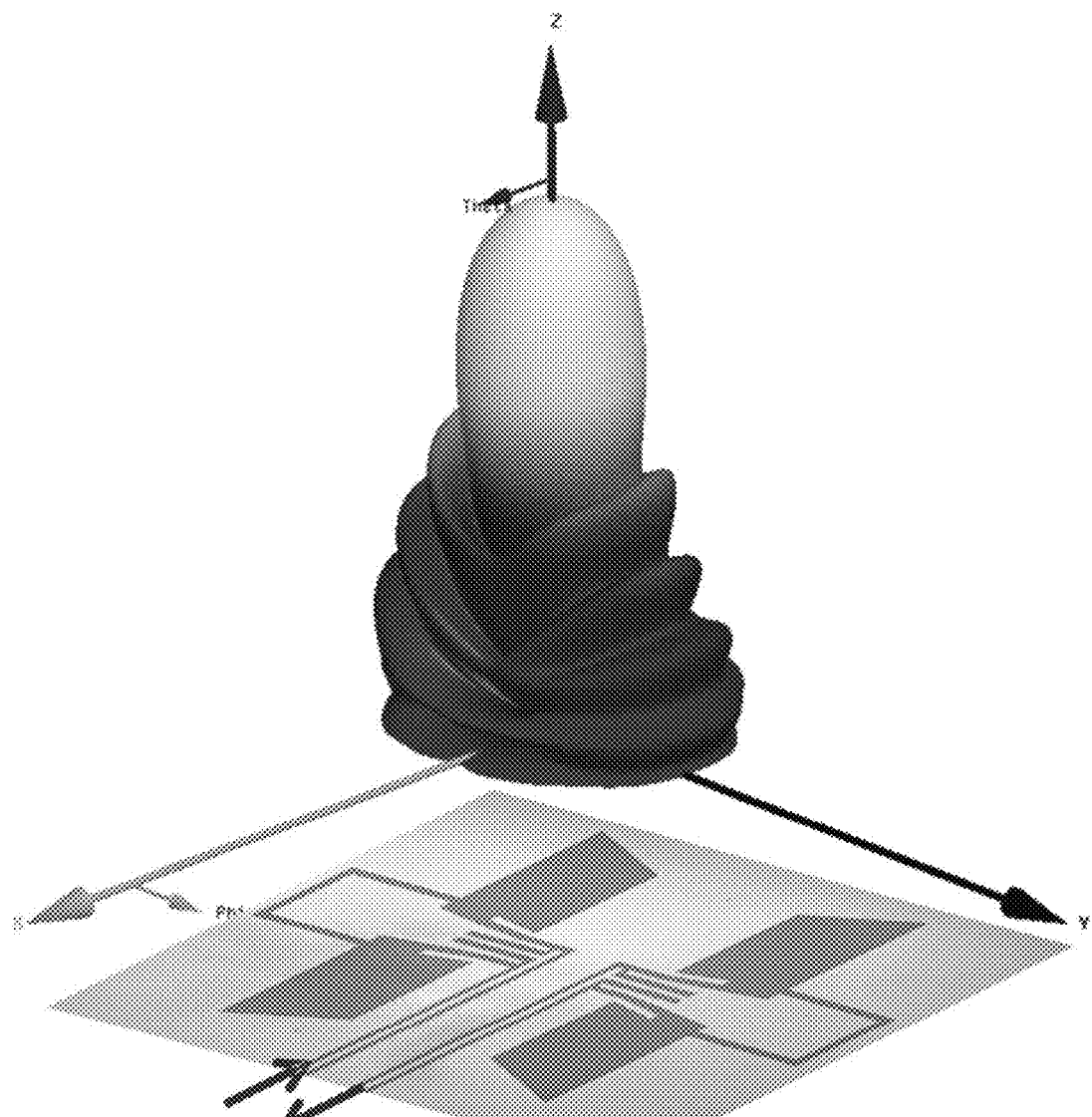
FIGS. 3-6 illustrate simulated radiation and/or reception properties (at the midband) of the differential non-contact probe-antenna pair of an illustrative embodiment of the test setup of FIG. 1.
Figure 4:
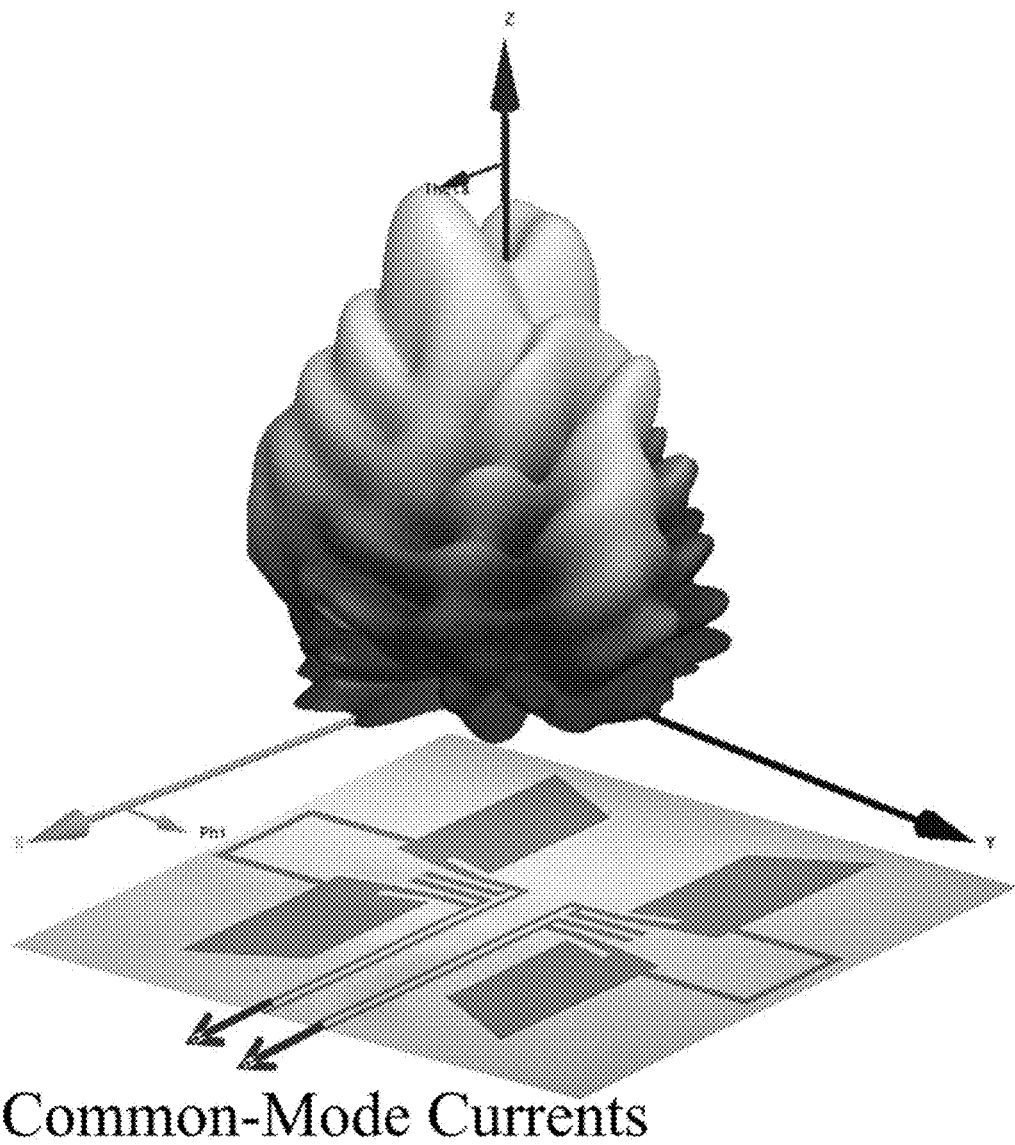
Figure 5:
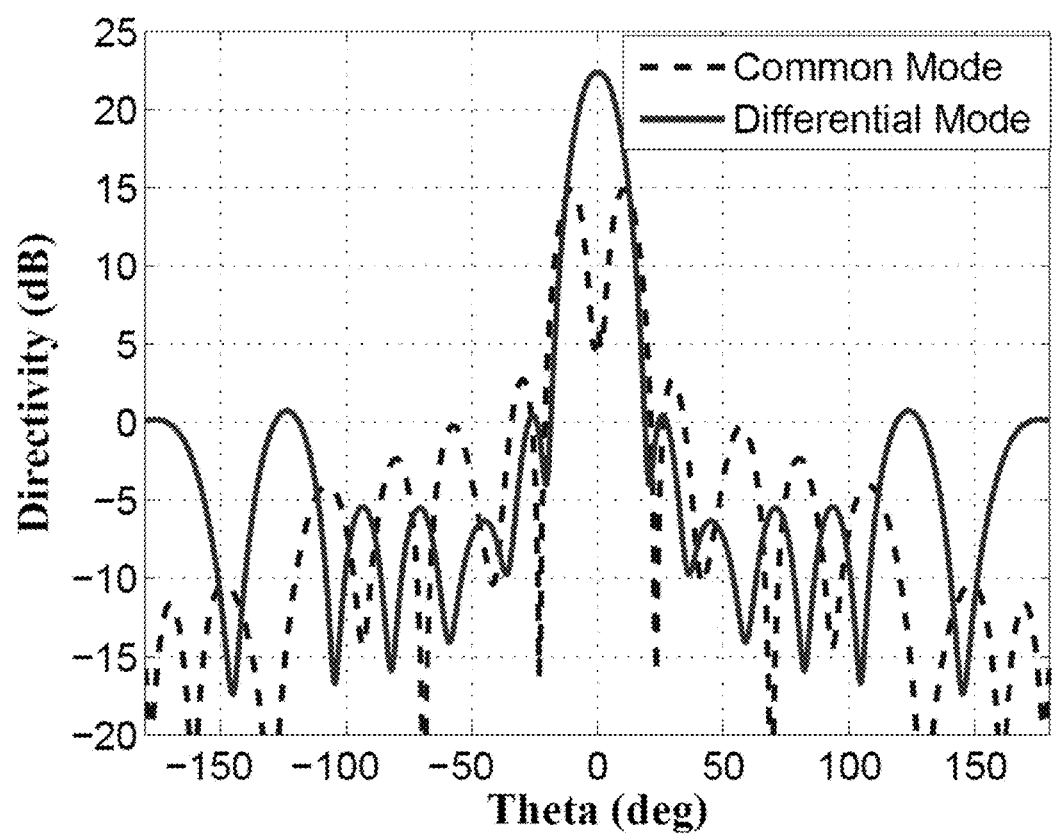
Figure 6:
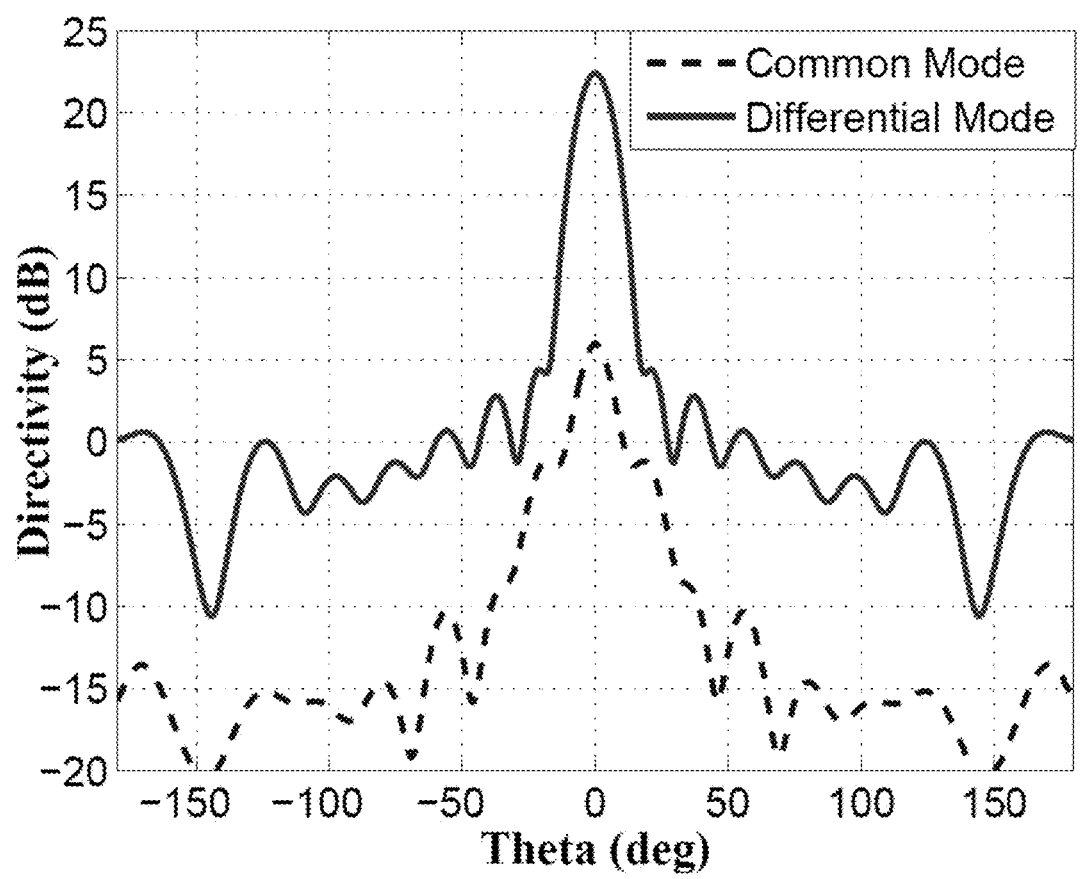

With reference to FIGS. 3-6, a highly-symmetric radiation pattern can be readily obtained, which facilitates efficient coupling with the quasi-optical components in the test setup. FIGS. 3-6 illustrate simulated radiation properties (at the midband) of the differential non-contact probe-antenna pair 30 integrated on a 1.5 mm diameter lens. FIG. 3 illustrates a differential mode three-dimensional (3D) polar plot of the radiation pattern when antenna ports (labeled as "Port-1" and "Port-2" in FIG. 2) are excited with 180° out-of-phase currents, illustrating a single-lobe, high-Gaussicity beam. FIG. 4 shows the corresponding common-mode 3D radiation pattern exhibiting a null in the broadside direction when antenna ports are excited in-phase. FIG. 5 plots the E-plane patterns of common- and differential-mode excitation, and FIG. 6 plots the corresponding H-plane patterns, illustrating the difference in directivity levels.

For characterization of active devices, two DC bias pads 28, 38 can also be integrated into the antenna pair 20, 30 to allow for individual biasing of the differential CPW lines 14, 16. Evidently, employing external DC contact probes is needed if it is desired to provide DC bias to the integrated circuits and transistor networks. Such low-cost DC probes are ubiquitously available. As shown in FIG. 1, the interrogating signals 46, 56 are injected and collected from the bottom side 58 of the wafer 10 carrying the DUT. Thus, the front side of the test wafer 10 can be easily accessed by DC probes from above, without disturbing the antenna operation.

The intrinsic 180°-hybrid mode capability of the balanced on-chip antennas (baluntennas) are due to the distinct radiation characteristics of the common and differential mode excitations. As seen in both 3D polar plots in FIGS. 3 and 4, and the E-plane patterns in FIG. 5, the in-phase currents fed into antenna ports yield a null in the broadside direction as opposed to the single-lobed beam radiated when the ports are excited 180° out-of-phase. Moreover, the change in the overall directivity of the resulting beam in H-plane is shown in FIG. 6, indicating over 25 dB isolation between the common and differential modes. As such, the combination of the quasi-optical link and the differential non-contact antenna behaves as a quasi-optical/THz-frequency 180°-hybrid with high isolation. Consequently, pure differential-mode signals can be excited in the on-wafer dual-CPW ports, while suppressing the any common mode propagation, due to the orthogonal radiation properties of the two modes (common-mode versus differential-mode). For optimal signal coupling, the input impedance of the antennas is tuned with the aid of stubs 60 (labeled only in FIG. 2) around the feed area and the reactive part of the differential antenna impedance was minimized.

Owing to the high degree of suppression of the common-mode by employing the antenna characteristics, as illustrated with reference to FIGS. 3-6, the operation of the differential non-contact probe antenna can be described based on the 180°-hybrid operation and an assumption of pure differential-mode operation. In FIG. 2, the differential probe-antenna 30 is shown in order to illustrate the three-port operation. Here, the third port ("Port-3"), illustrated as the radiation port of the antenna, is akin to a Δ output of a 180°-hybrid. As such, the relation between the incident and reflected power waves at the Port-3 can simply be written as:

$$b_3 = b_1 - b_2 \quad (1)$$

$$a_3 = a_1 - a_2 \quad (2)$$

where $b_n$ represents reflected power waves and $a_n$ represents incident power waves at respective three ports ("Port-n=1, 2, 3"). Assuming a pure differential-mode:

$$a_2 = -a_1 \quad (3)$$

And for the on-wafer ports ("Port-1" and "Port-2"):

$$b_1 = S_{11}a_1 + S_{12}a_2 \quad (4)$$

$$b_2 = S_{21}a_1 + S_{22}a_2 \quad (5)$$

Combining Equation (3) with Equations (4) and (5) yields:

$$b_1 = S_{11}a_1 - S_{12}a_1 \quad (6)$$

$$b_2 = S_{21}a_1 - S_{22}a_1 \quad (7)$$

Thus, Equation (1) can be written as:

$$b_3 = (S_{11} + S_{22} - S_{12} - S_{21})a_1 \quad (8)$$

In addition, Equation (2) reduces to:

$$a_3 = 2a_1 \quad (9)$$

As such, the pure differential-mode signal returned to the VNA test port in terms of on-wafer scattering parameters is given by:

$$S_{33} = (S_{11} + S_{22} - S_{21} - S_{12})/2 \quad (10)$$

Using the above model based on pure differential-mode propagation on the test ports, a calibration procedure for the differential-mode non-contact probes is implemented, as described next.

For accurate on-wafer S-parameters measurements, the test bed is calibrated up to an on-wafer reference plane. To do so, the quick-offset-short calibration methodology utilized in Caglayan et al., "Non-contact probes for on-wafer characterization of sub-millimeter-wave devices and integrated circuits", IEEE Trans. on Microwave Theory and Techniques, vol. 62 no. 11, pp. 2791-2801 (September 2014) was also used for the differential mode non-contact probes.

Figure 7:
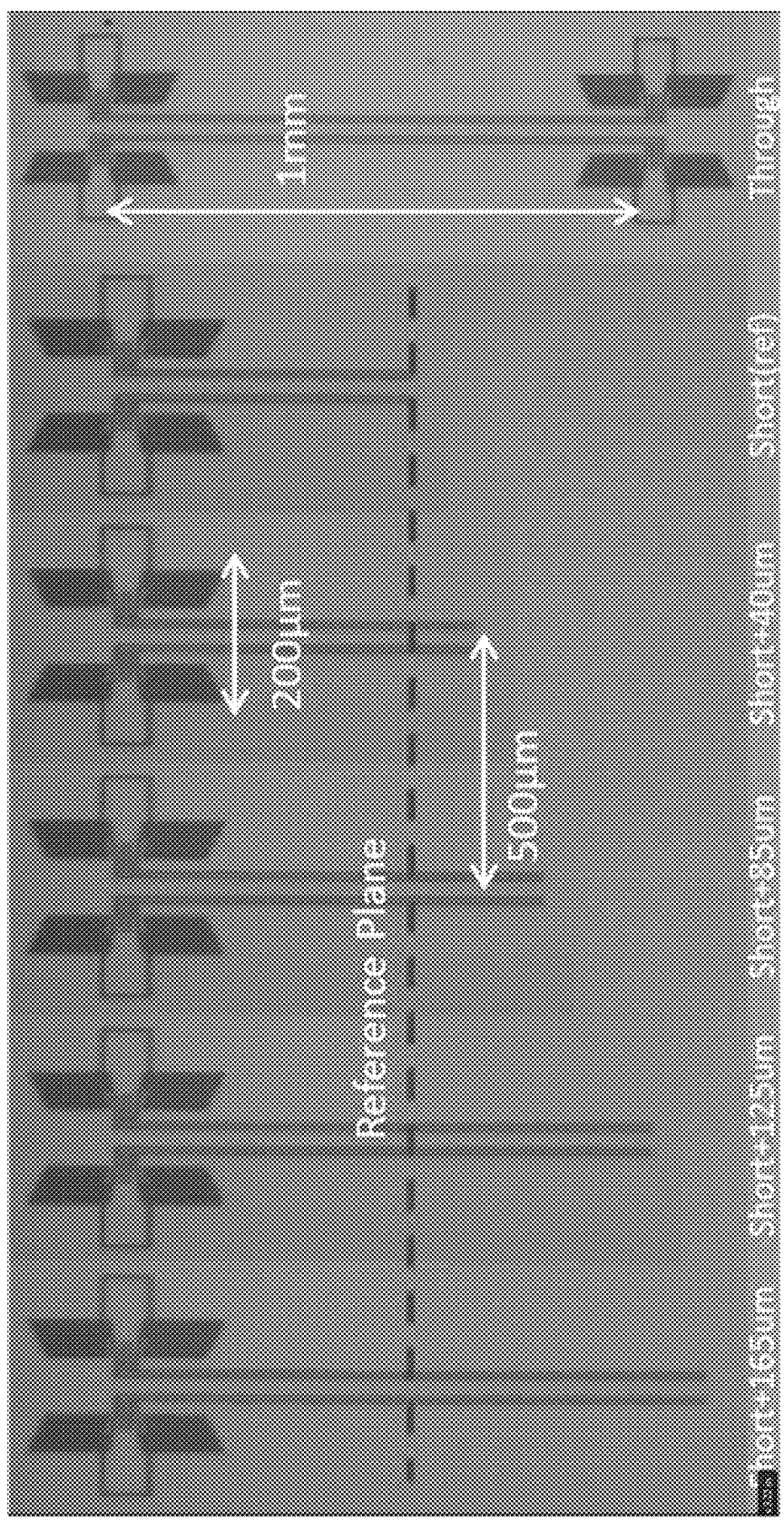
FIG. 7 illustrates an on-wafer calibration kit comprised of symmetric offset-short differential transmission line pairs.
Figure 8:
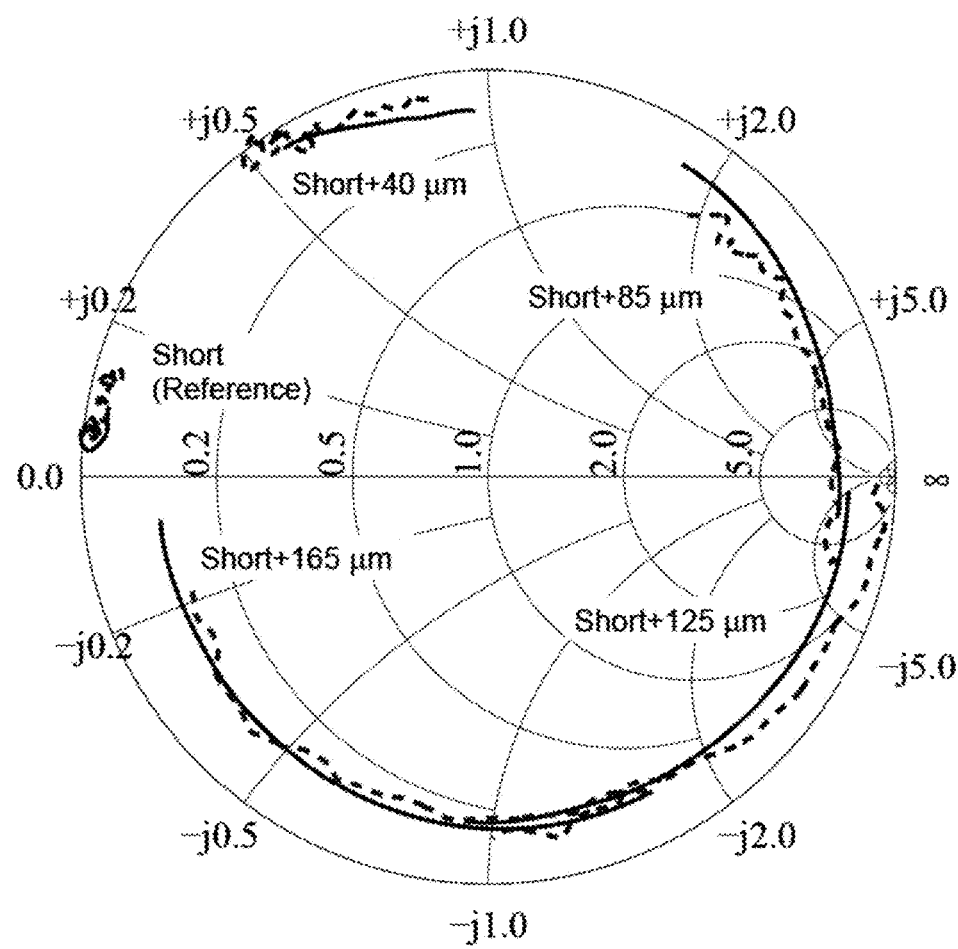
FIG. 8 presents a Smith chart showing computed impedances (solid lines) of the calibration standards and measured impedance values (dashed lines) for each standard.

With reference to FIGS. 7 and 8, to this end, an on-wafer calibration kit, comprised of symmetric offset-shorts (i.e., same offset for each port for each standard, as shown as in FIG. 7) and the simple through standard was fabricated on the same high-resistivity Silicon wafer along with a number of calibration verification devices. The standards seen in FIG. 7 and test devices were fabricated 220 μm apart from each other to provide isolation. Since this particular calibration methodology requires full-knowledge of the calibration standards, these standards were simulated using the full-wave electromagnetic analysis software Ansys HFSS v.15Sss.

All the on-wafer simulations should be performed with quasi-TEM propagation in anti-symmetric mode. After obtaining the scattering matrices, they were reduced to single-ended form using Equations (1)-(10) under the pure differential-mode assumption. In other words, two-port scattering matrix for one-port standards was converted to a single reflection term while four-port scattering matrix of the through standard was reduced to a two-port scattering matrix.

Following calibration, the standards were measured again using the calibration in-place. Repeated measurements of these standards can be used to assess the validity of the calibration since the error terms were computed via a least-squares fitting (non-linear) of an over-determined system that requires redundant number of calibration standards. As shown in the Smith Chart of FIG. 8, computed impedances of the calibration standards are in good agreement with re-measured impedance values for each standard, illustrating the experimental validation of the calibration procedure.

Figure 9:
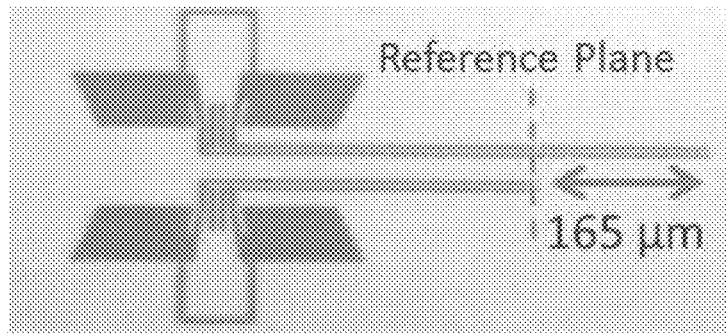
FIGS. 9-15 present simulation and experimental results as described herein.
Figure 10:
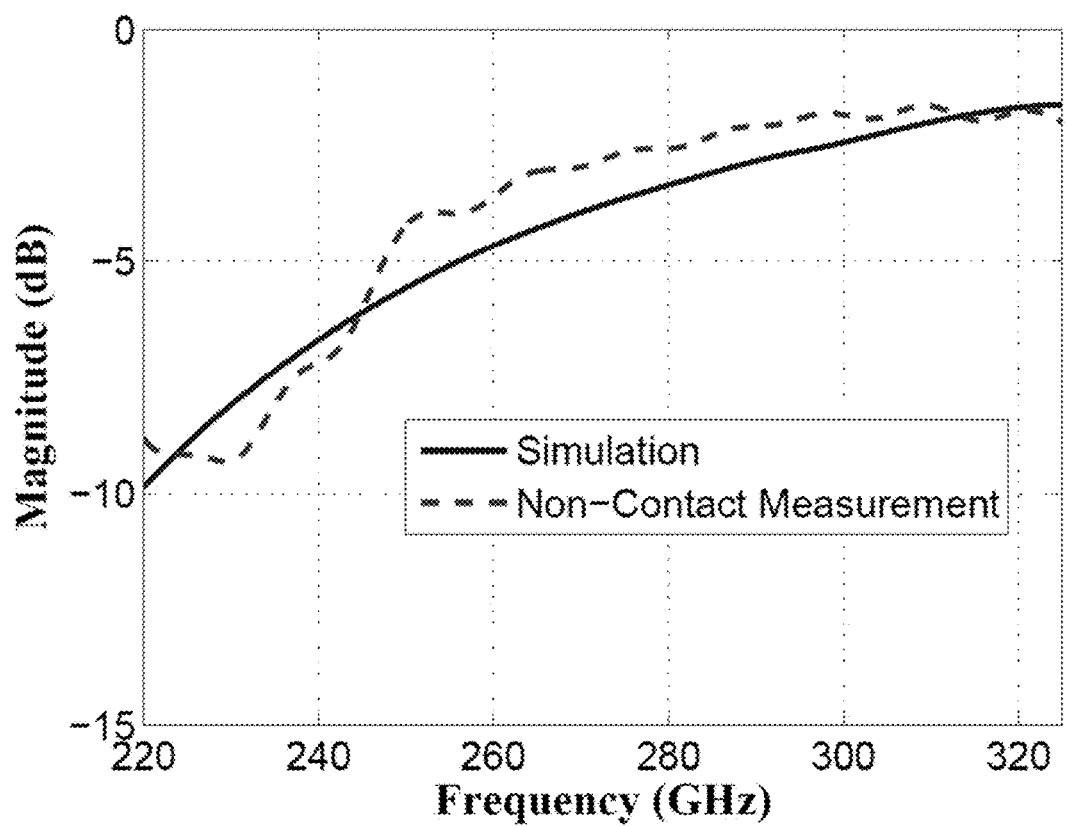

With reference to FIGS. 9 and 10, the assumption of pure differential-mode operation was tested next, via measurement of an unbalanced one-port device after the aforementioned calibration to demonstrate the common-mode suppression by the antenna. For this purpose, the one-port calibration standard shown in FIG. 9 is considered with a 165 μm line offset between the two coplanar, on-wafer ports. As seen in Smith Chart in FIG. 8, the phase shift between the signals reflected from the shorted ports with 165 μm line difference is observed to be close to 180 degrees at 220 GHz. As such, the reflection ($S_{11}$) is computed to decrease substantially towards 220 GHz. As shown in FIG. 10, the measured return signal demonstrates good agreement with the simulated results, verifying both calibration as well as the common-mode suppression.

To further demonstrate the efficacy of the non-contact differential-mode probes, in the following two-port H-band (220-325 GHz) measurements using the non-contact differential probes are next described. These measurements directly demonstrate full two-port measurements (pure differential-mode) using non-contact probes.

Figure 11:
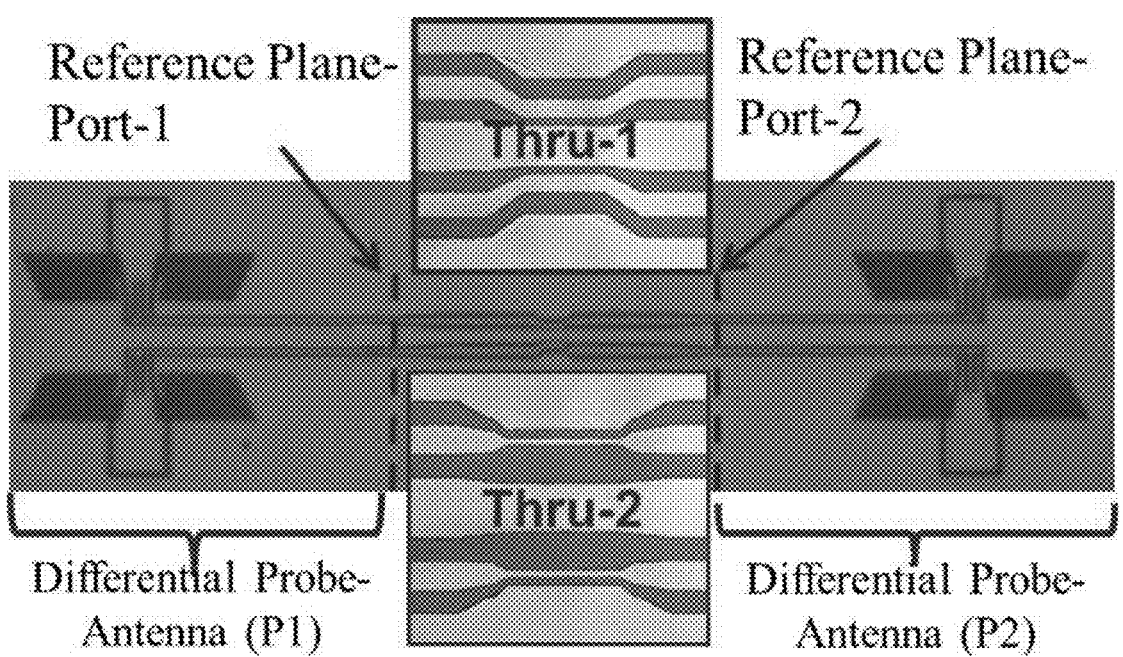
Figure 12:
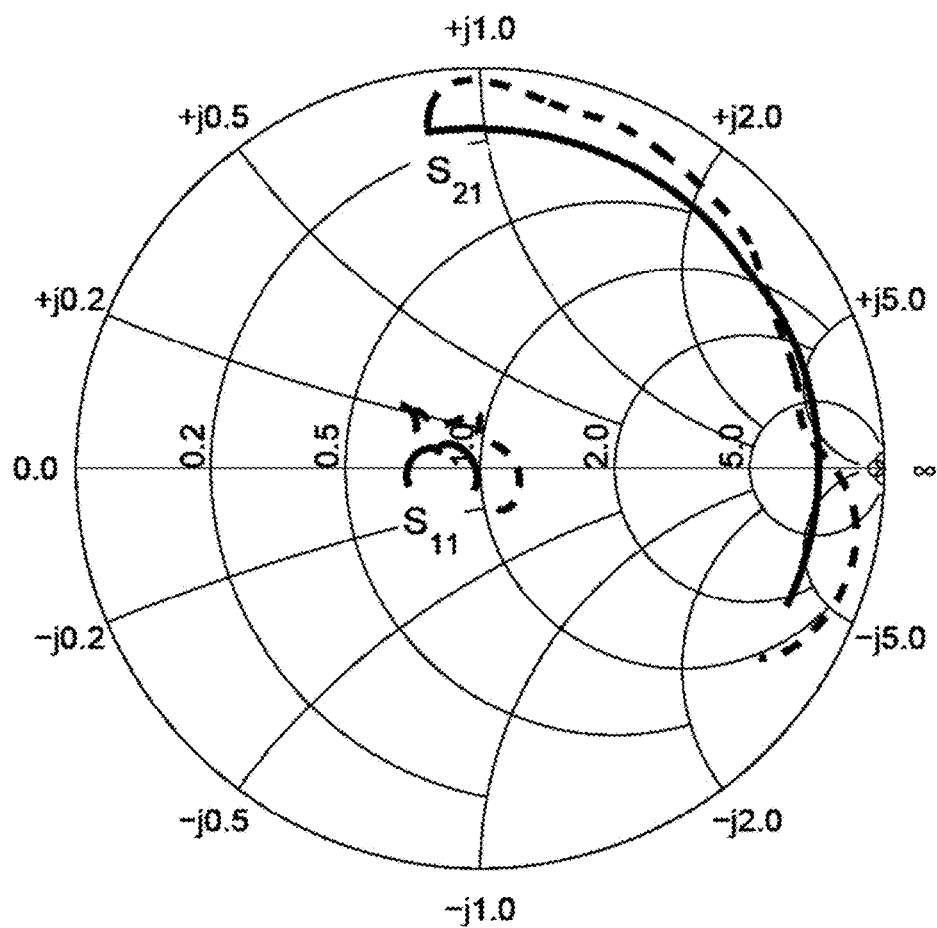
Figure 13:
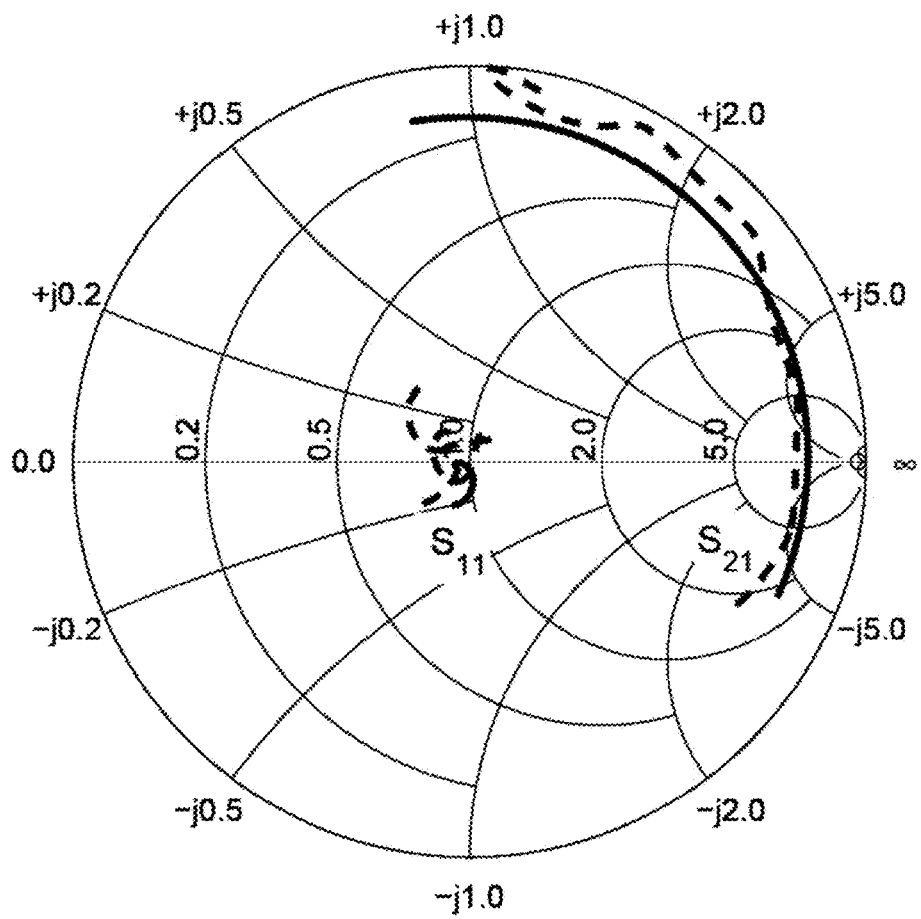

With reference to FIGS. 11-13, in order to verify the accuracy of the novel differential non-contact probes, several two-port verification devices were characterized in the 220-325 GHz. To do so, first, two "delay line" standards shown in FIG. 11 were considered. These topologies are among the standard layouts of the six-step process for external parasitic extraction of typical high-frequency HEMT (High Electron Mobility Transistor) structures. See Karisan et al., "Lumped-element equivalent circuit modeling of millimeter-wave HEMT parasitics through full-wave electromagnetic analysis," IEEE Trans. on Microwave Theory and Techniques, vol. 64, no. 5, pp. 1419-1430, 2016. As shown in the Smith Charts of FIGS. 12 and 13, there is very good agreement between the measured (dashed) and the calculated (solid) responses of the differential delay line standards. It is also noteworthy that the simulations were performed using four on-wafer ports, and converted to two single-ended ports using the pure differential-mode approach previously discussed.

Figure 14:
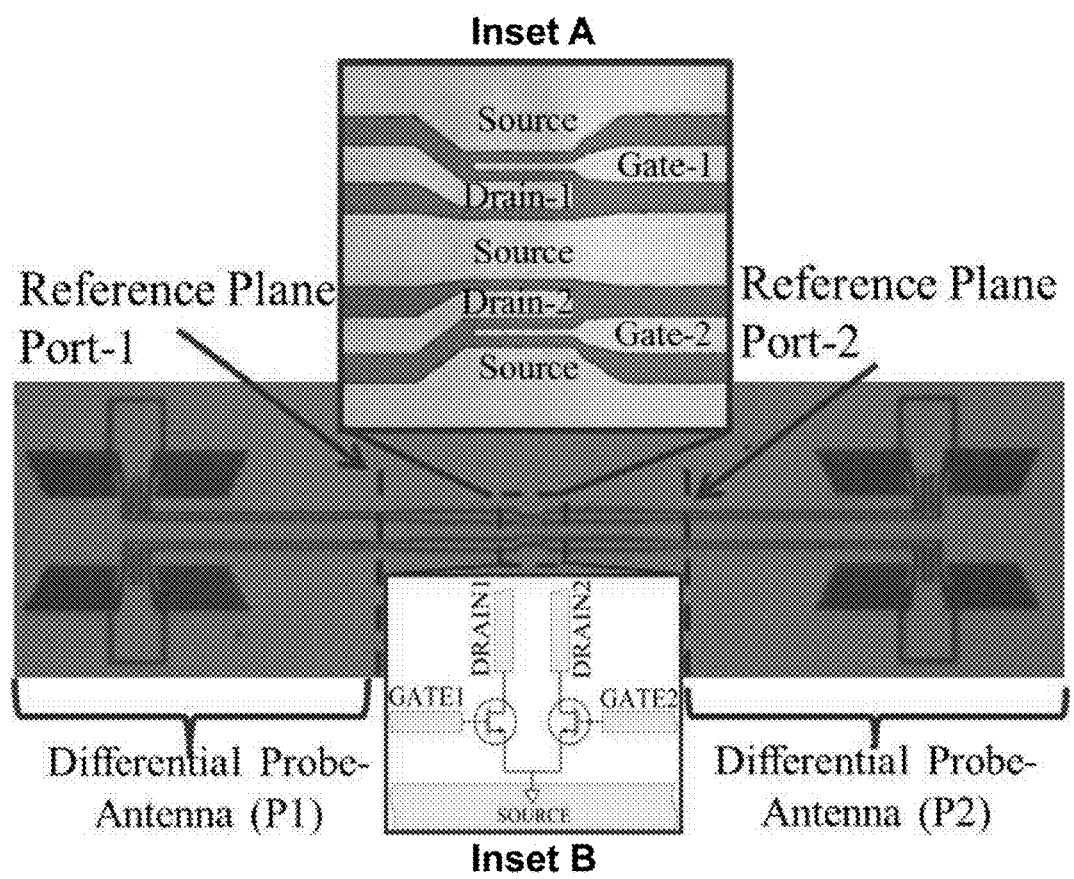
Figure 15:
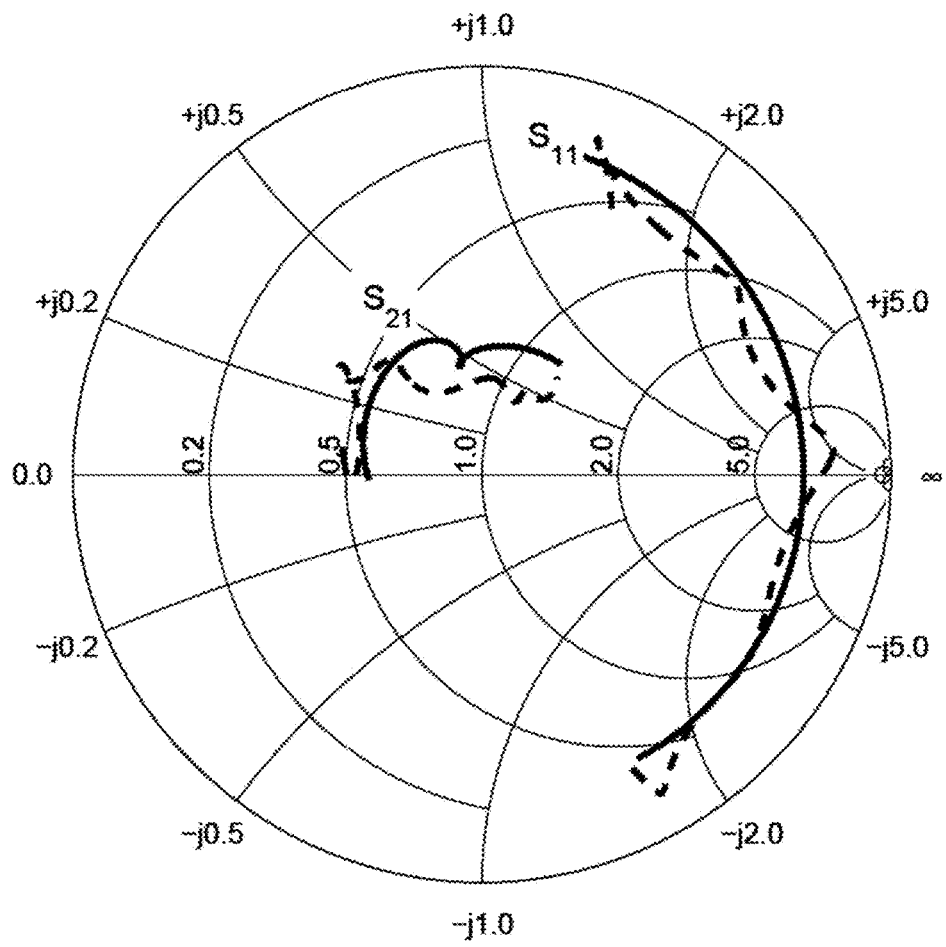

With reference to FIGS. 14 and 15, a contact lead topology representative of a cold HEMT structure was also considered. FIG. 14 shows a micrograph of the on-chip fixture, with an enlarged view of the cold HEMT structure shown in Inset A of FIG. 14. The equivalent circuit of the differential HEMT configuration is shown in Inset B of FIG. 14. As seen in the Smith chart of FIG. 15, again good agreement was obtained between the simulated S-parameters and the S-parameters measured using the non-contact differential probes. Since both test structures consist of only passive impedance steps and discontinuities, DC contact probes were not used for this validation.

Summarizing the foregoing illustrative test results, a differential-mode non-contact probe for characterizing on-wafer devices and integrated circuits was demonstrated for H-band (220-325 GHz) via full two-port calibration and measurement of verification structures including a HEMT access layout. Besides circumventing the typical drawbacks associated with contact probes, complexity of a balun-integrated probe tip is also avoided by simply modifying the on-chip probe-antennas. The disclosed differential non-contact probes provide advantages such as scalability from 90 GHz to beyond 1 THz, longevity (no wear/tear, unlimited number of measurements, etc.) and modularity, while facilitating differential on-wafer measurements well beyond 110 GHz.

The preferred embodiments have been described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An apparatus for performing terahertz (THz) or millimeter wave (mmW) characterization, the apparatus comprising:
   an integrated circuit including an on-chip device under test (DUT) and an on-chip test fixture including:
      a differential transmission line pair comprising parallel first and second transmission lines operatively coupled with the DUT wherein the first transmission line comprises two conductors and the second transmission line comprises two conductors;
      a first differential antenna pair connected with a first end of the differential transmission line pair and including a first antenna connected only with the first transmission line and a second antenna connected only with the second transmission line; and
      a second differential antenna pair connected with a second end of the differential transmission line pair and including a third antenna connected only with the first transmission line and a fourth antenna connected only with the second transmission line;
   a THz or mmW transmitter arranged to radiate a probe THz or mmW beam to the first differential antenna pair of the test fixture; and
   an electronic analyzer configured to receive a THz or mmW signal radiated by the second differential antenna pair of the test fixture responsive to the radiation of the probe THz or mmW beam to the first differential antenna pair of the test fixture.

2. The apparatus of claim 1 wherein:
   the first differential antenna pair forms a first balun that suppresses any common mode signal on the first end of the differential transmission line pair; and
   the second differential antenna pair forms a second balun that suppresses any common mode signal on the second end of the differential transmission line pair.

3. The apparatus of claim 2 wherein the on-chip fixture does not include any balun other than the first and second differential antenna pairs.

4. The apparatus of claim 1 wherein at least one of the first differential antenna pair and the second differential antenna pair includes two DC bias pads.

5. The apparatus of claim 4 wherein the integrated circuit is disposed on a wafer and the THz or mmW transmitter and the electronic analyzer are arranged to radiatively couple with the on-chip test fixture from a back-side of the wafer without contacting the integrated circuit.

6. The apparatus of claim 1 wherein the first and second transmission lines of the differential transmission line pair are coplanar waveguide (CPW) transmission lines.

7. The apparatus of claim 1 wherein the on-chip DUT includes a THz or mmW mixer, a THz or mmW voltage-controlled oscillator, or a THz or mmW amplifier.

8. A method for performing terahertz (THz) or millimeter wave (mmW) characterization of a device under test (DUT) comprising a component of an integrated circuit wherein the DUT is connected with an on-chip differential transmission line pair comprising parallel first and second transmission lines wherein the first transmission line comprises two conductors and the second transmission line comprises two conductors, the method comprising:
   exciting the DUT in differential mode by radiating a probe THz or mmW beam to a first on-chip differential antenna pair of the integrated circuit wherein the first on-chip differential antenna pair is connected with a first end of the on-chip differential transmission line pair and comprises a common mode-suppressing balun; and
   receiving a THz or mmW differential signal generated by the DUT in response to the exciting wherein the THz or mmW signal is received via radiation by a second on-chip differential antenna pair of the integrated circuit wherein the second on-chip differential antenna pair is connected with a second end of the on-chip differential transmission line pair and comprises a common mode-suppressing balun;
   wherein the excitation produces a first electric current in the first transmission line of the on-chip differential transmission line pair and a second electric current in the second transmission line of the on-chip differential transmission line pair having a 180° phase difference compared with the first electric current.

9. The method of claim 8 wherein:
the first on-chip differential antenna pair includes a first antenna connected only with the first transmission line of the on-chip differential transmission line pair and a second antenna connected only with the second transmission line of the on-chip differential transmission line pair; and
the second on-chip differential antenna pair includes a third antenna connected only with the first transmission line of the on-chip differential transmission line pair and a fourth antenna connected only with the second transmission line of the on-chip differential transmission line pair.

10. The method of claim 8 wherein:
the excitation of the DUT in differential mode does not use any electrical contact to the integrated circuit; and
the reception of the THz or mmW differential signal generated by the DUT in response to the excitation does not use any electrical contact to the integrated circuit.

11. An integrated circuit comprising:
an on-chip device under test (DUT); and
on-chip differential-mode non-contact probes including:
 a differential transmission line pair comprising parallel first and second transmission lines operatively coupled with the DUT;
 a first differential antenna pair connected with a first end of the differential transmission line pair and including a first antenna having a port connected only with the first transmission line and a second antenna having a port connected only with the second transmission line; and
 a second differential antenna pair connected with a second end of the differential transmission line pair and including a third antenna having a port connected only with the first transmission line and a fourth antenna having a port connected only with the second transmission line wherein the first differential antenna pair is configured to energize the first end of the differential transmission line pair in response to received THz or mmW radiation by the first antenna producing a first electric current in the first transmission line of the differential transmission line pair and the second antenna producing a second electric current in the second transmission line of the differential transmission line pair, wherein the first electric current and the second electric current have a 180° phase difference.

12. The integrated circuit of claim 11 wherein:
the first differential antenna pair comprises a first balun; and
the second differential antenna pair comprises a second balun.

13. The integrated circuit of claim 12 wherein the on-chip differential-mode non-contact probes do not include any balun other than the first and second differential antenna pairs.

14. The integrated circuit of claim 11 wherein:
the first differential antenna pair suppresses any common-mode signal on the first end of the differential transmission line pair; and
the second differential antenna pair suppresses any common-mode signal on the second end of the differential transmission line pair.

15. The integrated circuit of claim 11 wherein at least one of the first differential antenna pair and the second differential antenna pair includes two DC bias pads.

16. The integrated circuit of claim 11 wherein the first and second transmission lines of the differential transmission line pair are coplanar waveguide (CPW) transmission lines.

17. The integrated circuit of claim 11 wherein the on-chip DUT includes a THz or mmW mixer, a THz or mmW voltage-controlled oscillator, or a THz or mmW amplifier.

* * * * *